US009113928B2

(12) United States Patent
Hancock

(10) Patent No.: US 9,113,928 B2
(45) Date of Patent: Aug. 25, 2015

(54) COSMETIC SURGERY APPARATUS AND METHOD

(75) Inventor: Christopher Paul Hancock, Bristol (GB)

(73) Assignee: CREO MEDICAL LIMITED, Somerset (GB)

( * ) Notice: Subject to any disclaimer, the term of this patent is extended or adjusted under 35 U.S.C. 154(b) by 715 days.

(21) Appl. No.: 13/499,605

(22) PCT Filed: Oct. 4, 2010

(86) PCT No.: PCT/GB2010/001858
§ 371 (c)(1),
(2), (4) Date: Mar. 30, 2012

(87) PCT Pub. No.: WO2011/039522
PCT Pub. Date: Apr. 7, 2011

(65) Prior Publication Data
US 2012/0191072 A1    Jul. 26, 2012

(30) Foreign Application Priority Data
Oct. 2, 2009  (GB) .................................. 0917316.2

(51) Int. Cl.
*A61B 18/18*       (2006.01)
*A61B 18/00*       (2006.01)

(52) U.S. Cl.
CPC ....... *A61B 18/18* (2013.01); *A61B 2018/00464* (2013.01); *A61B 2018/00589* (2013.01); *A61B 2018/00642* (2013.01)

(58) Field of Classification Search
CPC ....... A61M 1/00; A61M 27/00; A61M 35/00; A61B 5/05; A61B 5/053; A61B 17/32; A61B 18/18; A61N 5/02

USPC .............................. 604/22, 319, 542; 606/32
See application file for complete search history.

(56) References Cited

U.S. PATENT DOCUMENTS 4,534,347 A    8/1985 Taylor
4,886,491 A    12/1989 Parisi et al.
(Continued)

FOREIGN PATENT DOCUMENTS

CN    1610566 A      4/2005
EP    0 331 313 A1   9/1989
(Continued)

OTHER PUBLICATIONS

Search Report, Chinese Patent Application No. 201080050772.6 dated Feb. 19, 2014.
(Continued)

*Primary Examiner* — Melanie Hand
(74) *Attorney, Agent, or Firm* — Arent Fox LLP

(57) ABSTRACT

The present invention provides surgical apparatus for liposuction in which microwave energy is delivered from a probe into a treatment region to perform a fat liquefying function or a haemostasis function. The apparatus is arranged such that an output microwave field automatically adopts a configuration suitable for the fat liquefying function or haemostasis function depending on the type of tissue encountered by the probe in the treatment region. In particular, by suitable selection of the frequency of the microwave energy, the difference in skin depth of the microwave energy in fat and blood may enable the microwave field to automatically switch its configuration between one suitable for fat liquefying and one suitable for haemostasis without any change required to the amount of microwave power or the energy profile delivered to the probe.

15 Claims, 6 Drawing Sheets

(56) References Cited

U.S. PATENT DOCUMENTS

| | | | |
|---|---|---|---|
| 5,295,955 | A | 3/1994 | Rosen et al. |
| 5,542,916 | A | 8/1996 | Hirsch et al. |
| 5,992,419 | A | 11/1999 | Sterzer et al. |
| 7,112,200 | B2 | 9/2006 | Cucin |
| 7,894,779 | B2 * | 2/2011 | Meiyappan et al. ............ 455/83 |
| 8,547,281 | B2 * | 10/2013 | Ryou et al. ............ 343/700 MS |
| 2003/0088235 | A1 | 5/2003 | Tazi |
| 2003/0120269 | A1 | 6/2003 | Bessette et al. |
| 2004/0073195 | A1 | 4/2004 | Cucin |
| 2004/0167516 | A1 | 8/2004 | Cucin |
| 2009/0062875 | A1 * | 3/2009 | Gelbart et al. .................... 607/7 |
| 2009/0125013 | A1 | 5/2009 | Sypniewski et al. |
| 2009/0192441 | A1 | 7/2009 | Gelbart et al. |

FOREIGN PATENT DOCUMENTS

| | | |
|---|---|---|
| JP | 02-185267 A | 7/1990 |
| WO | WO 96/34569 | 11/1996 |
| WO | WO 98/44968 A1 | 10/1998 |
| WO | WO 2005/115235 A1 | 12/2005 |
| WO | WO 2008/044013 A2 | 4/2008 |

OTHER PUBLICATIONS

Arye Rosen et al., RF/Microwave-Aided Tumescent Liposuction; IEEE Transactions on Microwave Theory and Techniques, vol. 48, No. 11, Nov. 2000, pp. 1879-1884.

International Search Report.

* cited by examiner

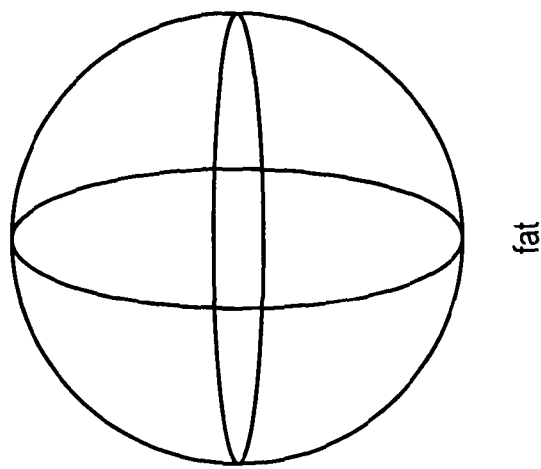
fat
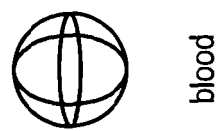
blood
FIG. 1

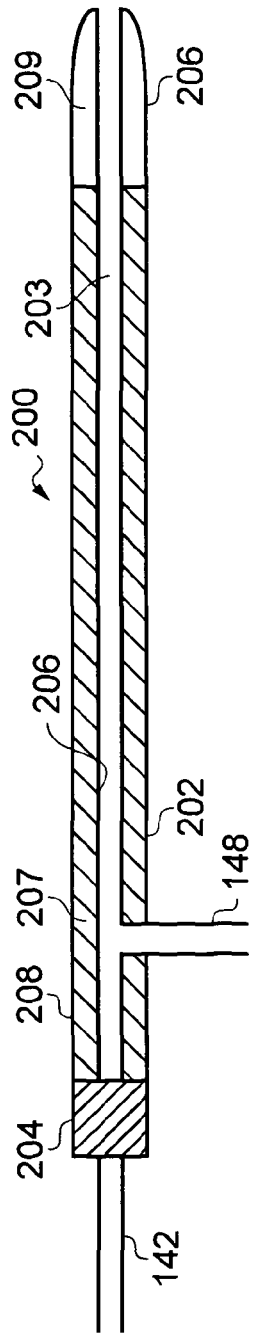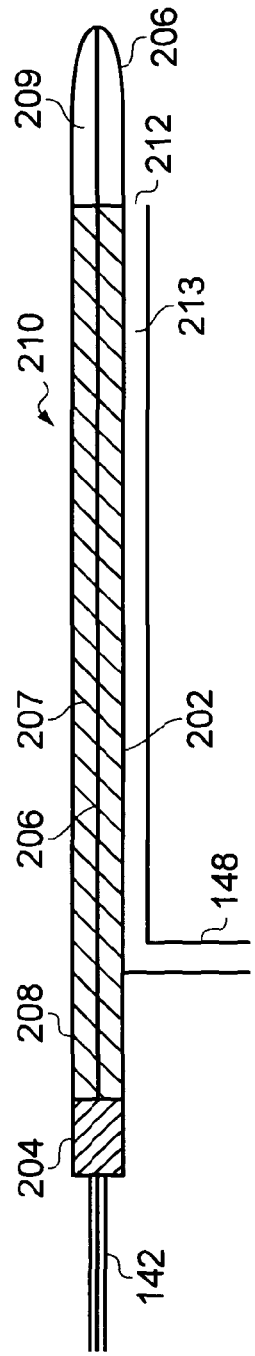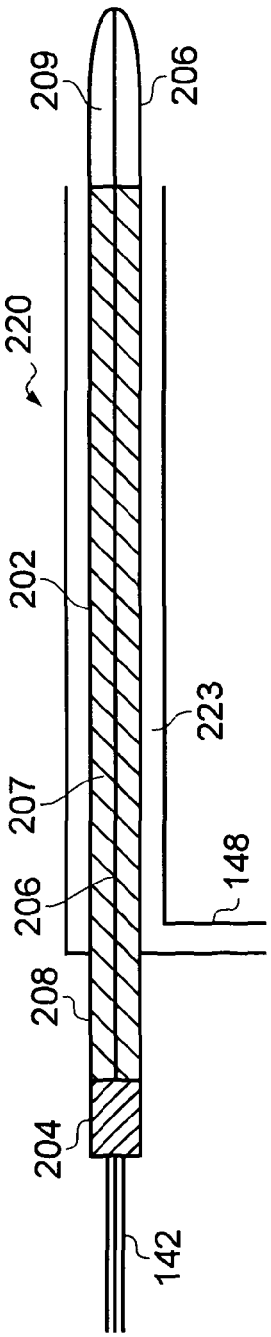

$d = \frac{(2n-1)\lambda}{4}$, n = 1, 2, 3...

$z = \frac{(2n-1)\lambda}{4}$, n = 1, 2, 3...

COSMETIC SURGERY APPARATUS AND METHOD

CROSS-REFERENCED TO RELATED APPLICATION

This application is a National Stage entry of International Application PCT/GB2010/001858, filed Oct. 4, 2010, which claims priority to British Patent Application No. 0917316.2, filed Oct. 2, 2009, each of the disclosures of the prior applications being hereby incorporated in their entirety by reference.

FIELD OF THE INVENTION

The invention relates to surgical apparatus and methods for performing liposuction. The invention may also assist pre- and post-treatment steps, e.g. tunneling to insert a suction device to a treatment site and/or performing tissue shrinkage in regions where fat has been removed. The invention may be used to remove fat from any one or more of the following regions of the body: tummy, breast, arms, neck, flanks, knees, hips, lips, bottom, thighs, abdomen, eyes, chin and other regions of the face.

BACKGROUND OF THE INVENTION

Liposuction concerns the removal of fat (adipose tissue) from under the skin. Usually fat is removed from the deep layer of subcutaneous tissue found in the hypodermis layer of the skin. Fat may be removed from the superficial layer of subcutaneous fat, but this is more difficult because that layer is denser than the deep layer and is tightly packed with nerves and blood vessels. Removing fat from the superficial layer risks damage to functional components of the skin, which can result in visible permanent irregularities, discolorations, and possibly skin necrosis.

In conventional liposuction procedures, a wetting solution or subcutaneous infiltration is used to promote ease of fat aspiration. Components of subcutaneous infiltrate include a base fluid of normal saline or lacerated Ringer's solution. Epinephrine is often added to this solution and lidocaine and/or bupivacaine may also be used for analgesia. Sometimes, gentamicin is added for infection prophylaxis and hyaluronidase to aid in lipolysis. Lidocaine toxicity must be avoided when carrying out the liposuction procedure in the traditional manner.

The sequence of filtration is normally such that infusion is generally done sequentially for each body area treated so as to minimise the overall fluid and pharmacologic load. It is normal to have a 10 to 20 minute latency period prior to aspiration to allow for epinephrine to have a maximal vasoconstrictive effect. This process can make the overall procedure unnecessarily time consuming.

Care must also be taken in conventional liposuction procedures to avoid perforation of the underlying fascia, peritoneum, and abdominal structures. Furthermore, the patient's fluid balance must be closely monitored when carrying out conventional liposuction. Blood loss caused when performing conventional liposuction may also be a major concern. There is a high risk of bleeding during and after the procedure. Medication to treat bleeding may be required.

U.S. Pat. No. 5,295,955 proposes using radiofrequency electromagnetic energy in combination with a conventional liposuction arrangement to heat fat at the treatment site so that it would soften and be easier to remove. However, it is essential to provide a polar liquid within the treatment site for the heating to be effective. Presence of this liquid increases patient discomfort. Moreover, it may be difficult to control excess heat generation which may cause undesirable collateral tissue damage.

U.S. Past. No. 6,920,883 proposes targeting electrical energy at a treatment region by providing active and return electrodes in close proximity to targeted tissue. An electrically conductive fluid is located between the electrodes to define a high frequency current path through targeted tissue. Current flow causes heating, softening or ablation of the targeted tissue.

U.S. Pat. No. 7,112,200 discloses a power-assisted liposuction device which is arranged to perform electro-cauterization. The liposuction device comprises an inner and outer cannula having active and return electrodes mounted thereon respectively to define a high frequency current path therebetween.

SUMMARY OF THE INVENTION

At its most general, the invention provides surgical apparatus for liposuction in which microwave energy is delivered from a probe into a treatment region to perform a fat liquefying function or a haemostasis function, the apparatus being arranged such that an output microwave field automatically adopts a configuration suitable for the fat liquefying function or haemostasis function depending on the type of tissue encountered by the probe in the treatment region. In particular, by suitable selection of the frequency of the microwave energy, the difference in skin depth of the microwave energy in fat and blood may enable the microwave field to automatically switch its configuration between one suitable for fat liquefying and one suitable for haemostasis without any change required to amount of microwave power or energy profile delivered to the probe. The invention may thus permit efficient fat liquefaction and haemostasis, which may obviate the need for additional fluid or medication, thereby improving patient comfort, and simplifying the surgical procedure, i.e. reducing the number of stages involved with the overall process, and making the procedure less time consuming. The new process may also reduce patient risk in terms of infection (the heat produced by the microwave energy may create a sterile environment), and also in terms of preventing excessive blood loss.

Furthermore, by suitable control of the output microwave field, the probe may perform further functions. For example, the probe may emit a microwave field for tightening tissue (e.g. collagen) in a region from which fat has been removed.

The apparatus may also be suitable for lipotunneling, where in the probe may emit a microwave field that facilitates insertion of the probe down a channel to the treatment region. The output microwave field in this case may act to ablate tissue to ease passage of the probe and/or to sterilise the channel during withdrawal of the probe. In the lipotunneling mode, the energy profile may be adjusted in accordance with the tissue type encountered at the end of the probe to enable the diameter of the channel to be uniform along the entire length of the channel. This may be achieved by tissue matching or power control based on information measured at the distal radiating end of the probe.

According to the invention there may be provided surgical apparatus for liposuction comprising: a microwave energy source arranged to output a controllable power level of microwave radiation; a probe for inserting to a treatment region in biological tissue, the probe including: an antenna connected to receive the output microwave radiation and arranged to emit outwardly a microwave radiation field to deliver microwave energy into the treatment region, and a conduit for conveying liquefied fat away from the treatment region; and a suction pump connected to the conduit; wherein the frequency of the microwave radiation and the controllable power level are selected such that the emitted microwave radiation field automatically adopts a first configuration when emitted into fat and a second configuration when emitted into blood, the microwave energy delivered by first configuration being for liquefying the fat and the microwave energy delivered by the second configuration being for coagulating the blood.

Herein, microwave radiation means electromagnetic radiation having a frequency greater than 300 MHz, e.g. between 1 GHz and 300 GHz. In particular embodiments, narrower frequency bands may be used. Thus, microwave radiation may also mean electromagnetic radiation having a frequency within any one or more of the following bands: 2.4 GHz to 2.5 GHz, 5.725 GHz to 5.875 GHz, 14 GHz to 14.5 GHz, 24 GHz to 24.25 GHz, 30 GHz to 32 GHz, 45 GHz to 47 GHz, 60 GHz to 65 GHz, and 74 GHz to 78 GHz. Even more specifically, microwave radiation may also mean electromagnetic radiation having a spot frequency of any one of more of the following frequencies: 2.45 GHz, 5.8 GHz, 14.5 GHz, 24 GHz, 31 GHz, 46 GHz and 61.25 GHz.

The microwave energy source may be any device or group of components capable of delivering a stable supply of microwave radiation. Preferably the source includes a stable oscillator (e.g. voltage controlled oscillator or a dielectric resonator oscillator) whose signal is amplified by a suitable power amplifier (e.g. one or more MMIC amplifiers, an arrangement of GaAs or GaN devices or the like). The oscillator may include a phase locked loop to minimise drift in the output frequency. The source may include a variable attenuator connected between the oscillator and the amplifier to control the output power level. A switch, e.g. a PIN diode switch, may be connected between the oscillator and the amplifier to permit the source signal to be modulated, e.g. to operate in a pulsed fashion or another modulation format, i.e. monopulses, ramps, etc. If the variable attenuator is suitably responsive, it may also perform the function of the switch.

The probe may be an elongate hand held unit of a suitable size for insertion into the human or animal body. For example, the probe may resemble a conventional cannula, i.e. a tubular body open at a distal end. For fine treatment, the outer diameter of the tubular body may be less than 2 mm. For treatment of large volumes, the outer diameter of the tubular body may be 10 mm or more.

The antenna may comprise a coaxial feed structure comprising an inner conductor separated from an outer conductor by a dielectric, and an aerial that terminates the coaxial feed structure at a distal end of the probe. In one embodiment the dielectric may be air, wherein spatial separation of the inner and outer conductors is achieved using an arrangement of insulating spacers (e.g. made from a low loss material arranged e.g. as thin slices spanning between the inner and outer conductor). The microwave field is radiated by the aerial. The coaxial feed structure conveys microwave power delivered to the probe to the aerial. The probe may include a connector at the proximal end of the coaxial feed structure that is adapted to transfer microwave power to and from a conventional coaxial power or transmission line. The connector may be an SMA connector or the like. This enables the probe to be connected to the source by a flexible microwave or RF cable assembly, which facilitates maneuverability during treatment. The coaxial feed arrangement, used to enable the microwave power to enter the structure, may extend longitudinally, i.e. along the same axis as the probe, or may be arranged to be at an angle to the probe, i.e. offset from e.g. orthogonal to the length of the probe shaft.

The aerial may be at the distal end of the probe. It may be a blunt rounded member, e.g. shaped to emit an omni-directional microwave radiation field. Alternatively, it may be tapered, e.g. in a cone-shape, to emit a more focussed microwave radiation field. A focussed electromagnetic field may be useful when performing liposuction on small structures or in environments containing densely packed blood vessels. Furthermore, if the antenna is used for collagen tightening or lipotunneling as discussed below, a focussed electromagnetic field provides better control. The shape of the aerial may be modelled, e.g. using electromagnetic or thermal field simulation tools, to ensure generation of a suitably shaped field. Similarly, the aerial may be shaped so that its impedance is similar to the impedance of the biological matter (e.g. fat, blood, collagen) it will be exposed to in use. This may reduce energy wasted due to excessive reflected signals at the interface between the aerial and the tissue. For example, the aerial may have an impedance similar to the impedance of blood to ensure efficient transfer of energy into blood to effect coagulation. In embodiments used for collagen tightening, the aerial may have an impedance similar to collagen for a similar reason.

The conduit may be a passageway extending along the probe from one or more openings. The openings may be at the distal end of the probe or at the sides of the probe near to the distal end. The openings may be configured in a manner similar to a conventional cannula. The conduit may be extended alongside the coaxial feed structure. Alternatively, the conduit may comprise an annular passage around the outside of the coaxial feed structure.

In one embodiment, the conduit may be integrated with the antenna. For example, the conduit may be a hollow tube in the inner conductor of the coaxial feed structure. This arrangement offers the advantage of a compact system. It is achievable because the skin depth of the microwave energy proposed herein in a good conductor is small enough for an inner conductor to be hollow without substantially affecting the energy conveyed. A further advantage occurs because the coaxial feed structure is not perfectly lossless. Any heat generated by losses in the feed structure may heat the fat conveyed in the conduit to maintain it in its liquefied state. Blockages in the conduit and the use of conventional wetting solution may thus be avoided.

The conduit may include a plurality of exit passages for efficient extraction of liquefied fat. Where the conduit is integrated with the antenna, each exit passage may extend outwardly from the axis of the coaxial feed structure, and act as a coaxial stub extending therefrom. To prevent the exit passages from causing losses in the antenna, each exit passage may extend an odd number of quarter wavelengths away from the axis of the coaxial feed structure before it terminates at a short circuit between the inner and outer conductor. In this way, a maximal field can be ensured in the coaxial feed structure. The plurality of exit passages may be spaced from one another along the axis of the feed structure. The separation between adjacent exit passages may be a multiple of half wavelengths. The advantage of using a plurality of exit passages is that this arrangement may assist the flow or passage of fat along the structure or may prevent the build up of pressure or a blockage occurring somewhere within the tube.

In one embodiment, the conduit extends along the axis of the coaxial feed structure and includes an outlet on the axis. In this embodiment, the coaxial feed structure may be side-fed rather than end-fed, i.e. a microwave connector may be arranged at an angle to the coaxial feed structure, i.e. at 90° to the length of the structure.

The antenna may include an integral impedance transformer, e.g. to match a distal section (which may have an impedance of 50Ω for receiving microwave power from a conventional 50Ω cable assembly) with a proximal section having a lower impedance, e.g. 20Ω or the like, arranged to match with the impedance of biological tissue, e.g. blood or collagen. The impedance transformer may comprise a section of the coaxial feed structure having a length that is a odd multiple number of quarter wavelengths in which the relative relationship between the inner and outer diameters of the inner and outer conductors is arranged to provide that section with an impedance that transforms the source impedance (e.g. 50Ω) to the impedance of the distal section. Having a distal section with a lower impedance may enable the diameter of a conduit formed through the inner conductor to be larger for a given instrument diameter. This is a consequence of the relation for impedance of the coaxial feed structure:

$$Z = \frac{138}{\sqrt{\varepsilon_r}} \log \frac{b}{a},$$

where Z is the impedance of the coaxial body, $\varepsilon_r$ is the relative permittivity of the dielectric material separating the inner and outer conductors, a is the outer diameter of the inner conductor and b is the inner diameter of the outer conductor. If b and $\varepsilon_r$ remain constant, a decrease in Z is achieved by an increase in a, which in turn provides for a greater cross-sectional area for the conduit, which may assist the flow of fat along the inside of the structure.

The suction pump may be a conventional pump used in normal liposuction procedures.

In another embodiment, the antenna may comprise a hollow waveguide structure, i.e. with no centre conductor. For example, a cylindrical or rectangular waveguide section may be used to replace the coaxial system described above. The waveguide section may be loaded or filled with a magnetic or dielectric material with a relative permeability or permittivity greater than 1 to reduce the size of the structure such that it may be attractive to perform certain clinical procedures, i.e. a cylindrical structure may be loaded in such a manner that the outside diameter of the overall structure may be less than 2 mm, thus making it attractive to perform surgery on fine tissue structures, i.e. removal of fat from the lips. In this embodiment, a separate channel may be provided to extract the fat, e.g. an additional outer sleeve may be attached to the waveguide structure or a separate tube (or plurality of tubes) that run along the length of the waveguide structure may be attached to the body of the waveguide. Alternatively, the structure may be designed such that the dominant mode of propagation is set up when the waveguide is completely or partially filled with fat. If it is assumed that a cylindrical structure is used, and that the lowest loss propagation mode, i.e. the $TE_{11}$ mode, is set up, then the required diameter of the waveguide structure may be calculated as follows:

$$D = \frac{2.4485c}{\pi f_0 \sqrt{\varepsilon_r \mu_r}},$$

where: D is the diameter of the inner wall of the waveguide structure, the constant 2.4485 is derived from Bessel functions for the particular $TE_{11}$ mode of operation, c is the speed of light (approximately $3 \times 10^8$ ms$^{-1}$), $f_0$ is the frequency of operation, $\mu_r$ is the relative permeability of a magnetic loading material, $\varepsilon_r$ is the relative permittivity of a dielectric loading material. For example, if a cylindrical structure is designed with a frequency of operation of 46 GHz and a dielectric material with a relative permittivity of 25 is used to load the waveguide, then a structure with a 1 mm inside diameter may be implemented. Also, due to the skin depth being less that 1 μm at this frequency of operation, the overall diameter of the applicator is approximately 1 mm. In this particular arrangement, a rod of hard dielectric, i.e. low loss microwave ceramic, may be used to implement the design, where said rod may be coated with a thin layer of silver to form the waveguide wall. This probe structure may be particularly beneficial for use in certain cosmetic treatments where fine tissue structures are involved, i.e. where the removal of small quantities of fat and subsequent skin tightening is required.

As mentioned above, a refinement to this particular antenna structure may be to use the biological material being removed from the body (e.g. fat) as the dielectric loading material. In this particular instance, the structure will be set up to propagate the dominant mode of propagation when the waveguide cavity is filled with biological tissue. A further enhancement to this idea may be to partially fill the waveguide with a solid dielectric and/or magnetic loading material and then fill the remaining section of the waveguide cavity with the extracted biological tissue. In this particular instance, the relative permittivity and/or the relative permeability of the fixed loading material(s) will be chosen such that the structure is optimised in terms of diameter (or rectangular cross section or the critical dimension associated with the particular geometry used) and the propagation of the dominant (or other) mode set up within the guide.

As the hollow waveguide may be cut-off, i.e. will not propagate energy into tissue, if no fat or other loading material is present inside the cavity, the device may initially operate at a start-up frequency to allow the waveguide to propagate energy and then adjust to a treatment frequency once the waveguide cavity is loaded with fat (or other biological tissue). The start-up frequency may be greater than the treatment frequency. The idea of loading the cavity with fat also enables the applicator to be used directly to remove fat (or other biological tissue) and overcomes the need to use a separate external channel for fat extraction.

A particular advantage of the invention is that the frequency of the microwave radiation and the controllable power level may be the same in the first and second configurations. That is, no adjustment to the apparatus may be needed between ordinary warming of fat and special heat sealing of broken blood vessels. This advantage is made possible by selecting the frequency of microwave energy (which is related to the skin depth of the microwave radiation in fat and blood) and the power level delivered such that the first and second configurations cause a temperature increase in fat and blood respectively, the temperature increase caused by the second configuration in blood being greater than the temperature increase caused by the first configuration in fat. For example, the temperature increase in fat caused by the first configuration may be less than 3° C., wherein the temperature increase in blood caused by the second configuration may be 10° C. or more, e.g. 20° C. or more.

The difference in skin depth in fat and blood at the frequencies considered herein means that the microwave energy may be delivered into a smaller volume in the second configuration than the microwave energy delivered in the first configuration. Thus, if the same power is delivered in the first and second configurations, the heating effect will be higher in the second configuration because the energy is concentrated into a smaller volume.

In practice, the delivered power may be reflected by different amounts due to the different impedance values for fat, blood, and other biological tissue of interest; this corresponds to an impedance mismatch between the antenna and the contact tissue. Such reflections may be taken into account when selecting the output power level of the microwave energy source. Alternatively, the apparatus may monitor and adjust the power delivered to the probe. For example, the apparatus may include a detector for detecting microwave power reflected back from the treatment region and a controller for adjusting the controllable power level of microwave radiation based on changes in the detected reflected microwave power.

A change in reflected power, e.g. a change in the magnitude of a microwave signal travelling back from the interface between the probe and biological tissue, may indicate a change in the type of material present at the distal end of the probe. The controller may be arranged to recognise certain expected changes, e.g. from fat to blood, and automatically adjust the controllable power level based on the recognition.

The detector may also be arranged to detect forward power delivered to the probe. The controller may thus be able to determine the amount of power being delivered to the biological tissue. The controller may be arranged to adjust the controllable power level of microwave radiation based on the detected forward and reflected microwave power to deliver microwave energy according to a predetermined energy delivery profile. The controller may be arranged to select the predetermined energy delivery profile from a plurality of predetermined profiles based on changes in the detected reflected microwave power.

Each predetermined energy delivery profile may by linked with a tissue type. For example, an energy delivery profile for blood may be arranged to ensure delivery of enough power to cause a rise in temperature that would seal a broken blood vessel.

The controller may be arranged to measure the magnitude (and/or phase) of the impedance of the biological tissue at the distal end of the probe and to select a predetermined energy delivery profile according to the measured impedance.

To ensure accurate detection, the apparatus may be arranged to isolate the reflected power from the forward power. For example, the apparatus may include a circulator connected between the source, probe and detector, wherein a forward path for microwave energy from the source passes from a first port to a second port of the circulator, a reflected path for microwave energy from the probe passes from the second port to a third port of the circulator, and the detector includes a first directional coupler connected to couple power output from the third port of the circulator.

To detect forward power, the detector may include a second directional coupler connected to couple power input to the first port of the circulator.

To improve isolation between the forward and reflected paths, one or more additional circulators may be connected between the second directional coupler and the circulator.

This invention is not limited to the use of one or more circulators to provide the necessary isolation between the forward going and reflected signals, i.e. a directional coupler with a high value of directivity, e.g. a waveguide coupler, may be used.

The microwave energy source may have an adjustable output frequency. For example, there may be more than one oscillator in the source, each oscillator being selectively connectable to the amplifier. Alternatively, the source may include a variable frequency generator. The frequency may be selected before use, e.g. depending on the tissue to be treated or the size of the treatment region. The controller may be arranged to adjust the frequency in use, e.g. based on changes in the reflected microwave power.

In a development of the invention, the controllable power level of microwave radiation may be adjustable to cause the emitted microwave radiation field to adopt a third configuration when emitted into collagen, the third configuration being for tightening the collagen. The apparatus may be thus be applied to ligaments, tendons or muscle after fat removal to shrink and denature collagen to enable skin tightening to occur.

In a further development, the apparatus may assist in the tunneling process, where the probe is percutaneously inserted through a small incision in the skin. In this development, the microwave energy source may be activated during insertion, whereby a microwave radiation field is emitted by the antenna into the tissue structures (or anatomical layers) that exist between the surface of the skin and the region of the body whereby the fat is to be removed. The emitted field may facilitate insertion and seal the track towards the treatment region. This may reduce patient discomfort and recovery time, e.g. prevent blood loss.

The apparatus may include an impedance matching mechanism arranged to match the impedance of the antenna in the probe with the biological tissue at the distal end of the probe during tunneling. The impedance matching mechanism may also operate during liposuction and/or skin tightening. The impedance adjustment and/or energy profile adjustment based on variations in impedance presented to the antenna may be used to ensure that a track of ablation with a constant diameter is created during the tunneling procedure.

The invention may also be expressed as a method of performing liposuction comprising: inserting a probe to a treatment region in biological tissue, the probe including: an antenna connectable to receive microwave radiation output by a microwave energy source; and a conduit for conveying liquefied fat away from the treatment region; activating the microwave energy source, whereby the antenna emits outwardly a microwave radiation field to deliver microwave energy in the treatment region; activating a suction pump connected to the conduit; and selecting the frequency of the microwave radiation and the output power level of the microwave energy source such that the emitted microwave radiation field automatically adopts a first configuration when emitted into fat and a second configuration when emitted into blood, the microwave energy delivered by first configuration being for liquefying the fat and the microwave energy delivered by the second configuration being for coagulating the blood.

The method may include, after liposuction is completed, adjusting the output power level of microwave radiation to cause the emitted microwave radiation field to adopt a third configuration when emitted into collagen, the third configuration being for tightening the collagen to prevent the formation of layers of skin (skin flaps) or wrinkles. The first, second and third configurations may be arranged to cause a localised temperature increase in fat, blood and collagen respectively, the temperature increase caused by the third configuration in collagen being greater than the temperature increase caused by the second configuration in blood, and the temperature increase caused by the second configuration in blood being greater than the temperature increase caused by the first configuration in fat. For example, the third configuration may cause the temperature of collagen to increase to 70° C. or more. The second configuration may cause the temperature of blood to rise to 45° C. or more. The first configuration may cause the temperature of fat to rise to 40° C.

The method may include activating the microwave energy source during insertion of the probe into biological tissue to facilitate tunneling of the probe to the treatment region. The method may include impedance matching the impedance of the antenna in the probe with the biological tissue at the distal end of the probe during insertion of the probe into biological tissue.

The focussed and controlled heat produced by the probe may also be used to provide a sterile environment or to self-sterilise the apparatus to prevent infection of the tissue that is in contact with the instrument. This may be an advantage over conventional methods of liposuction where the instruments may become infected during the procedure and this infection is transferred to the patient tissue.

BRIEF DESCRIPTION OF THE DRAWINGS

Examples of the invention are discussed below with reference to the accompanying drawings, in which:

FIG. 1 shows schematically (not to scale) the relative volumes of heated matter in blood and fat for the frequencies of microwave energy considered herein;

FIGS. 3A, 3B and 3C are schematic cross-sectional side views through probes suitable for use with the apparatus shown in FIG. 2;

DETAILED DESCRIPTION, FURTHER OPTIONS AND PREFERENCES

Figure 2:
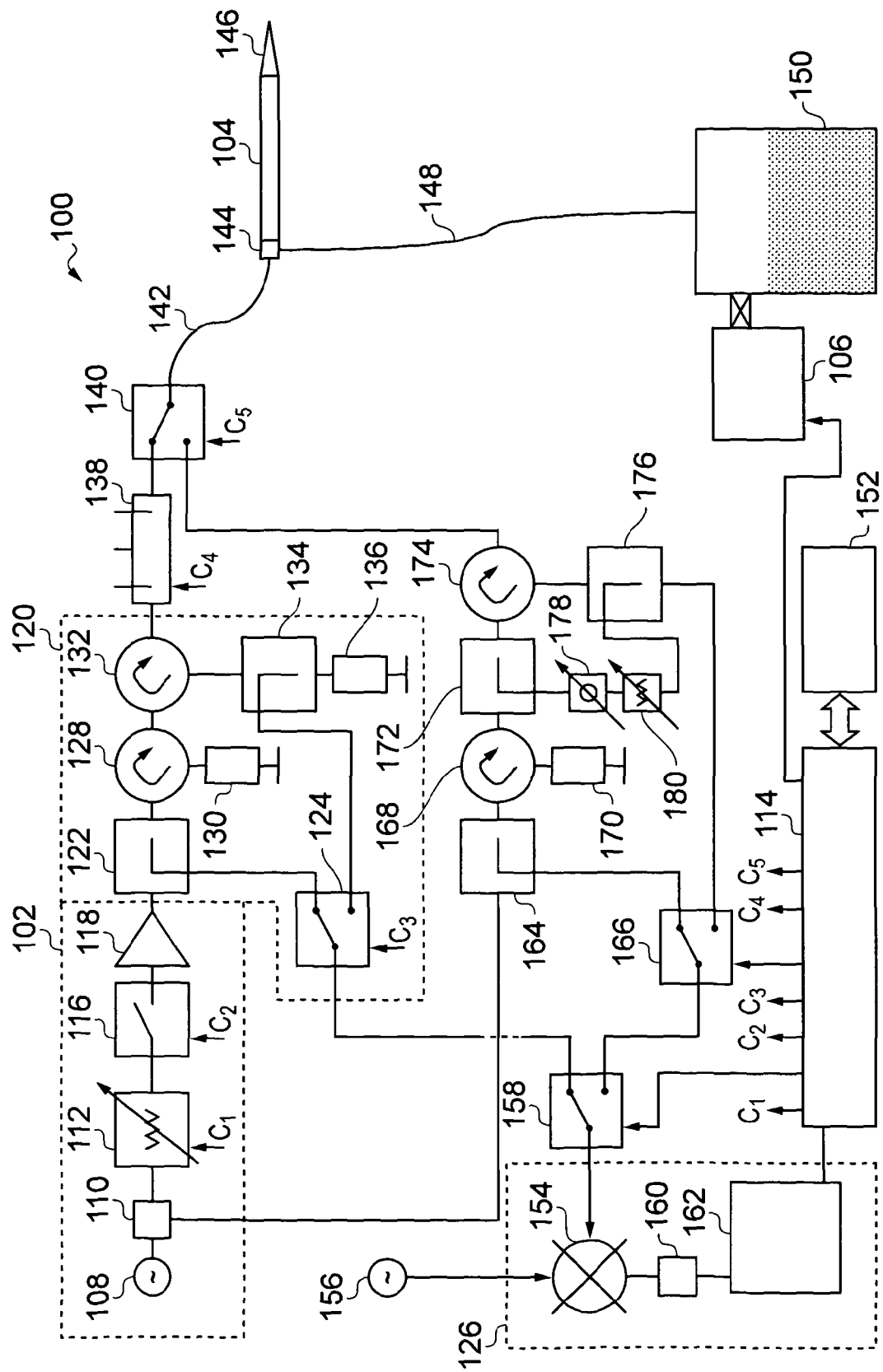
FIG. 2 is a block diagram showing surgical apparatus that is an embodiment of the invention.

When a conductive material is exposed to an electromagnetic field, it is subjected to a current density caused by moving charges. In solids, the current is limited by the collision of electrons moving in a network of positive ions. Good conductors, such as gold, silver and copper, are those in which the density of free charges are negligible, the conduction current is proportional to the electric field through the conductivity, and the displacement current is negligible with respect to the conduction current. The propagation of an electromagnetic field inside such a conductor is governed by the diffusion equation, to which Maxwell's equations reduce in this case. Solving the diffusion equation, which is valid mainly for good conductors, where the conduction current is large with respect to the displacement current, it can be seen that the amplitude of the field decays exponentially inside the material, where the decay parameter (skin depth) $\delta$ is:

$$\delta = \frac{1}{\sqrt{\frac{\omega\mu\sigma}{2}}},$$

where $\sigma$ is the conductivity of the material, $\mu$ is the permeability of the material, and $\omega$ is the radian frequency (i.e. $2\pi f$, where f is the frequency).

From this, it can be seen that the skin depth decreases when the frequency of the microwave energy increases as it is inversely proportional to the square root of this frequency. It also decreases when the conductivity increases, i.e. the skin depth is smaller in a good conductor than it is in another less conductive material.

Biological materials are not good conductors. They do conduct a current, but, because the losses can be significant, they cannot be considered as lossless materials. For most biological materials, the displacement current is of the order of the conduction current over a wide frequency range and the more general expression must be used to describe $\delta$:

$$\delta = \frac{1}{\omega}\left\{\frac{\mu\varepsilon}{2}(\sqrt{1+p^2}-1)\right\},$$

where $p = \dfrac{\sigma}{\omega\varepsilon}$ is the ratio of the amplitudes of the conduction current to the displacement current. These equations are strictly valid for solids limited by plane boundaries. They are also applicable to materials limited by curved boundaries when the curvature radius is more than five times larger than the skin depth. In other cases, a correction factor should be applied.

Knowledge of the skin depth enables selection of frequency to yield particular energy distributions in conductors and biological materials. For example, at a depth of 3δ, the field amplitude is only 5% of its amplitude at the interface, and the corresponding power is only 0.25%. At a depth of 5δ, the field amplitude reduces to 1% and the corresponding power to $1\times10^{-4}$%, i.e. 40 dB isolation.

The invention is based on the fact that the depth of penetration of a microwave field (i.e. electromagnetic field having a frequency in the range of between 1 GHz and 300 GHz) when energy propagates in biological tissue is modified by the dielectric properties of the tissue in such a manner that enables the fat to be gently heated whilst blood can be instantly coagulated and collagen can be rapidly tightened, i.e. by using relatively short, e.g. 50 ms, high amplitude, e.g. 80 W, pulses.

The depth of penetration of a microwave field, i.e. an electromagnetic radiation field having a frequency in the range 1 GHz to 300 GHz, by radiation into blood is much less that the depth of penetration of the same field into fat. Depth of penetration means the depth into matter by which the field has dropped by a factor of 1/e or has decreased to 37% of its initial value. For example, at 14.5 GHz, the depth of penetration into blood (1.6 mm) is approximately a factor of ten less than the depth of penetration into fat (12.2 mm). At 5.8 GHz the difference is a factor of 6.75, i.e. 6 mm into blood and 40.5 mm into fat. The effect of this on the volume in which power is dissipated is illustrated in FIG. 1. In blood the power is dissipated in a smaller volume that fat. As a consequence, the temperature change in blood is correspondingly higher for the same amount of microwave energy delivered.

This follows from the fact that it may be assumed that the microwave energy produces a spherical energy distribution, i.e. the volume of heated tissue V may be assumed to be:

$$V = \frac{4\pi\delta^3}{3},$$

where δ is the depth of penetration that is equal to radius of the sphere.

The depth of penetration into fat is 12.2 mm and 40.5 mm for 14.5 GHz and 5.8 GHz respectively. The volumes of a spheres with radiuses corresponding to these depths of penetration are 7,606 mm³ and 278,262 mm³ respectively. These volumes are small enough to be contained within a treatment region in which fat cells are to be broken down in a controlled manner to enable fast removal using a standard suction pump.

On the other hand, the depth of penetration into blood is 1.6 mm and 6 mm for 14.5 GHz and 5.8 GHz respectively. The volumes of a spheres with radiuses corresponding to these depths of penetration are 17 mm³ and 905 mm³ respectively. These volumes are small enough to enable the same power level to be used to raise the temperature of the blood such that instant coagulation occurs.

A system arranged to deliver microwave energy at a constant power level and frequency may thus act as a self-regulating haemostat to prevent excessive blood loss during a liposuction procedure. This is due to the fact that the same energy will be absorbed by a volume of blood that is 447 times less at 14.5 GHz and 307 times less at 5.8 GHz than the corresponding volume of fat.

A system based on 14.5 GHz energy may be used to remove fat from fine tissue structures, e.g. the neck, the eyes (lids), or the chin, and a system based on a 5.8 GHz energy source may be used to remove fat from larger tissue structures.

To effectively break down the walls of the fat, the required temperature elevation above body temperature may be as small as 2 or 3° C., whereas to be able to instantly coagulate blood, the temperature elevation above body temperature may be between 20° C. and 30° C. Depths of penetration that can enable temperature changes of this kind are of particular interest in the invention.

Table 1 provides details of depth of penetration into blood and fat and the volumes of tissue that will be instantly affected for a number of spot frequencies that are considered useful for implementation of the current invention. In each case there is an assumption that the shape of tissue affected by the radiation is a sphere and that the field has decreased to 37% of its maximum or initial value with the depth of penetration.

TABLE 1

Depth of penetration of 63% of the field and associated tissue volume affected by the field at this depth at various frequencies

| f (GHz) | δ (blood) (mm) | δ (fat) (mm) | V (blood) (mm³) | V (fat) (mm³) |
|---|---|---|---|---|
| 5.8 | 6.0 | 40.5 | 905 | 278262 |
| 14.5 | 1.6 | 12.2 | 17 | 7606 |
| 24 | 0.9 | 7.1 | 3.1 | 1499 |
| 31 | 0.69 | 5.5 | 1.4 | 697 |
| 46 | 0.48 | 4.0 | 0.5 | 268 |

This automatic blood coagulation or instant haemostasis feature may be advantageous for cosmetic surgeons and the patient, as it may obviate the need to inject or provide medication to the patient before or after performing the liposuction procedure to prevent bleeding. Furthermore, standard procedures often require water or saline to be introduced to help break down the fat, which can make the procedure messy, uncomfortable and time consuming. The controlled gentle energy delivery into fat described above may obviate the need for extra fluid.

FIG. 2 shows a block diagram of surgical apparatus 100 suitable for implementing the ideas discussed above. The apparatus 100 comprises a first (treatment) channel having a microwave energy power source 102 connected to deliver microwave energy to a probe 104. The probe 104 includes a conduit (not shown) for removing liquefied fat from a treatment site using suction provided by suction pump 106.

The source 102 comprises an oscillator 108, e.g. a voltage controlled oscillator or dielectric resonant oscillator, arranged to output a signal at a stable frequency, e.g. 14.5 GHz. The oscillator 108 may be connected to a stable crystal reference in a phased locked loop configuration (not shown) to keep its frequency steady. The output of the oscillator is connected to the input port of a power splitter 110 (e.g. 3 dB splitter), which separates the output signal between a treatment channel and a measurement channel (discussed below). The measurement channel may not be needed during the liposuction procedure, so the splitter 110 may be optional. The output from the splitter 110 on the treatment channel is received by a variable attenuator 112, whose function is to vary the amplitude of the signal under the control of control signal $C_1$ from controller 114 in order to adjustably control the overall output power level of the treatment channel. The output from the variable attenuator 112 is received by a switch 116 (e.g. a PIN diode switch), whose function is to modulate the signal under the control of control signal $C_2$ from the controller 114 in order to enable pulsed operation (or another modulation format, i.e. a triangular waveform or a ramp falling abruptly to zero once maximum value has been reached). The output from the switch 116 is received by a power amplifier 118 (e.g. an array of MMIC amplifiers), whose function is to amplify the power level of the signal to a level suitable for treatment. A particular embodiment of power amplifier 118 is a Triquint TGA4521-EPU MMIC, whose output is connected in cascade to the input of a higher power Triquint TGA4046-EPU MMIC. The TGA4521-EPU device is capable of producing a gain of 15 dB and a power level of 23 dBm (200 mW) when driven into saturation using an appropriate drive signal at a frequency of up to 47 GHz, and the TGA4046-EPU device is capable of producing a gain of 16 dB and a power level of 33 dBm (2 W) when driven into saturation using an appropriate drive signal at a frequency of up to 46 GHz. In this embodiment, the system may be driven using source oscillator 108 outputting a frequency of 46 GHz and an output power of 2 dBm to enable 2 W of power to be produced at the output of the second MMIC connected in the cascade arrangement. Source oscillator 108 may be a device available through Castle Microwave Ltd, part number: OFD-KF460105-01, which is a dielectric resonator oscillator that is capable of producing an output power level of up to 5 dBm, has a mechanical tuning range of ±25 MHz, a frequency stability of ±4 ppm/degree C., and phase noise of −95 dBc/Hz at 100 kHz offset.

As explained above, control of the power input to the amplifier 118 using the variable attenuator 112 enables control of the output power level.

The output power level may be dynamically controlled based on information from a detector 120 that is connected on the treatment channel between the source 102 and the probe 104. In this embodiment, the detector 120 is arranged to detect both forward signals from the source 102 to the probe 104 and reflected signals travelling back from the probe 104. In other embodiments the detector may only detect reflected signals. In yet further embodiments the detector may be omitted altogether.

The detector 120 comprises a forward directional coupler 122 connected to couple power from the output of the amplifier 118. The coupled port of the coupler 122 is connected to a switch 124, whose function is to select either the forward coupled or reflected coupled power under the control of control signal $C_3$ from controller 114 to be conveyed for measurement by a heterodyne detector 126. The output of the forward directional coupler 122 on the treatment channel is received by the first port of a first circulator 128, whose function is to isolate the reflected signals travelling back from the probe 104 from the source 102. Forward signals on the treatment channel travel from the first port of the first circulator 128 to its second port, where they are output. Any reflected signals received at the second port of the first circulator 128 travel to the third port and are output into a power dump load 130. The output from the second port of the first circulator 128 is received by the first port of a second circulator 132, whose function is to convey the reflected signal towards a reflected directional coupler whilst isolating the reflected signal from the forward signal. Forward signals on the treatment channel travel from the first port of the second circulator 132 to its second port, where they are output. Reflected signals from the probe 104 are received at the second port of the second circulator 132, from where they travel to the third port and are output. The output of the third port of the second circulator 132 is received by a reflected directional coupler 134, whose function is to couple power from the reflected signal. After passing through the coupler 134, the reflected signal is absorbed in a power dump load 136. The coupled port of the reflected power coupler 134 is connected to the switch 124 to be conveyed to the heterodyne detector 126 when selected. It is advantageous to use two circulators in this configuration, but this invention is not limited to the use of two, i.e. one, three, or more may be used.

The output from the detector 120 on the treatment channel is received by an impedance tuning mechanism 138, whose function is to match the impedance of the components on the treatment channel with the impedance of the probe 104 when it is in tissue to facilitate efficient power transfer into tissue. The impedance tuning mechanism 138 may be optional. In this embodiment, the impedance tuning mechanism 138 comprises a cavity with three stubs insertable therein under the control of control signal $C_4$ from controller 114. The impedance tuning mechanism 138 may be as described in WO 2005/115235. The impedance tuning mechanism may be operational only during insertion (tunneling) of the probe as discussed below. The impedance adjusting mechanism need not be limited to this configuration, i.e. it could comprise a single or plurality of power varactor or power PIN diodes connected to a microstrip or other transmission line between the output of the power generator and the antenna, or a variable (or adjustable) length of microstrip (or stripline) configured as a variable tuning stub that can also be moved along a constant impedance microstrip or other transmission line between the output of the generator and the antenna. All tuning positions may be achieved by a change in length of the variable stub and its movement along the microstrip or coaxial line may be between limited to up to half the loaded wavelength at the frequency of interest.

The output from the impedance tuning mechanism 138 is received by a switch 140, whose function is to select either a treatment channel signal or a measurement channel signal for input to the probe 104 under the control of control signal $C_5$ from controller 114. This switch may be a waveguide switch, a power varactor/PIN diode switch, a coaxial switch, or the like.

The output signal from the switch 140 is conveyed to the probe 104 by a flexible transmission cable (e.g. coaxial cable) that is terminated in a connector 144 on the probe 104. The connector 144 transfers the signal to an antenna (not shown) which includes an aerial 146 arranged to emit a microwave radiation field from the distal end of the probe 104. The frequency of the microwave radiation and the power level of the signal sent to the probe are selected such that the microwave radiation field adopts a configuration in fat (adipose tissue) that causes a rise in temperature sufficient to break cell walls over a suitable volume in the treatment region, whereby the fat is liquefied.

A conduit (not shown) in the probe 104 includes one or more openings at the distal end of the probe 104. The proximal end of the conduit is connected via a transport pipe 148 to a storage vessel 150. A suction pump 106 applies a suction force via the transport pipe to the conduit whereby liquefied fat at the distal end of the probe 104 is sucked into the storage vessel 150. The suction pump 106 is controlled by controller 114.

A user can interact with the controller 114 via user interface 152, which may be a touch screen display, a membrane keypad and a LCD/LED display, or the like.

The heterodyne detector 126 comprises a mixer 154 arranged to receive a reference signal from a fixed frequency source 156 and a measurement signal from the detector 120 or the detector on the measurement channel (discussed below) via switch 158. After mixing, the output signals are passed through a filter 160 to allow only the lower frequency difference signal to be available for measurement of magnitude and optionally phase using a digital signal processor 162 in a conventional manner. A hardware solution may also be used to enable the magnitude and phase information to be extracted, i.e. a quadrature I-Q mixer may be used. The measurement result is sent to the controller 114, where it is used in subsequent operations associated with the control of the device.

In use, the measurements obtained from the signals produced by detector 120 provide a indication of the amount of power being delivered to the tissue, e.g. fat, blood, collagen, etc. Changes in the delivered power may be indicative of changes in the type of tissue at the distal end of the probe 104. The controller 114 may select an energy delivery profile based on the measurements. Different types of energy profile are discussed below with reference to FIG. 4.

Fundamentally, it is the combination of the microwave frequency and output power level that determines the volume and amount of heating that occurs in the treatment region. At the microwave frequencies discussed herein, the depth of penetration into blood is much less than that into fat, so for a given output power level the amount of heating in blood (or temperature elevation of blood) is automatically greater. This facilitates quick sealing of broken blood vessels encountered during treatment.

The amount of energy that is reflected by blood may be different to the amount of energy reflected by fat. The detector may detect this change and the controller may be arranged to recognise that a given change corresponds to the appearance of blood. Although the microwave field configuration automatically changes for blood, the change in the amount of reflected energy may affect the amount of energy transferred into the blood. The reflection coefficients for electromagnetic radiation emitted into fat and blood with a frequency in the range 1 GHz to 300 GHz differ significantly. For example, if we assume that an energy delivery antenna has a characteristic impedance of 50Ω and the operating frequency is 14.5 GHz, the reflection coefficient for fat is 0.56 compared to 0.05 for blood. The apparatus may be adjustable to account for this. For example, the controller may monitor the amount of delivered energy using the signals from the detector and adjust the output power level if necessary. Dynamic impedance matching may also be implemented to ensure that the reflection coefficient remains as close as possible to zero during the procedure, regardless of any changes in reflection coefficient due to impedance mismatch between the end of the probe and the contact tissue.

The frequency of the oscillator 108 may be adjustable, e.g. depending on the size of the treatment region. At higher frequencies the depth of penetration of the field configurations for both fat and blood are smaller, but the relative difference appears to remain unchanged.

The apparatus may be used in a method of performing an integrated liposuction and skin tightening procedure. In this procedure, the probe is inserted into the subcutaneous fat and energy is delivered to the fat to gently heat it and cause it to be liquefied. The liquefied fat is removed from the body along the conduit contained within the probe, using the suction pump and storage vessel. Any blood flow caused by the rupture of blood vessels during the procedure is instantly ceased due to the fact that the high microwave frequency produces a small depth of penetration of the energy into blood compared to that of subcutaneous fat, e.g. 1 mm compared to 12 mm, to enable blood to be instantly coagulated, i.e. to provide an automatic haemostasis feature. When the fat has been drained, the probe may be relocated to the region of the skin containing collagen and the energy profile is modified to allow the temperature to be quickly increased to up to 80° C. to enable skin tightening to be performed. The detection system may permit reliable and accurate monitoring of the process of collagen denaturation through changes in the reflection coefficient between the distal end of the probe and the collagen.

A particular application of the apparatus may be in a method of performing an integrated liposuction and skin tightening procedure on fine tissue structures. In this application the probe is inserted into a fine tissue structure. Energy is then delivered into the fine tissue structure using a first mode of operation in which the energy profile is suitable for gently heating fat cells within the fine tissue structure to cause the fat to liquefy. A suitable energy profile may be one in which energy is delivered by continuous wave transmission to the probe at a power of 10 W or less. Alternatively, the energy may be delivered by a short duty cycle pulsed transmission, i.e. a pulsed transmission with a 10% or lower duty cycle. A combination of these two energy transmission methods may be utilised. Once the fat has been liquefied, a small amount of fat is removed from the fine tissue structure along the conduit contained within the probe, using the suction pump and storage vessel. When the fat has been drained, energy is delivered into the fine tissue structure using a second mode of operation in which the energy profile is suitable for heating collagen to a temperature of up to 80° C. to enable collagen tightening to be performed. A suitable energy profile may be one in which energy is delivered by continuous wave transmission to the probe at a power of 10 W or greater. Alternatively, the energy may be delivered by a longer duty cycle pulsed transmission, i.e. a pulsed transmission with a 10% or greater duty cycle. A combination of these two energy transmission methods may be utilised. The energy profiles in the first and/or the second mode of operation may include features such as ramping, one or more steps, or a combination of these features. The shape of the energy profiles in the first and/or the second mode of operation is not limited to a continuous wave or a square-wave pulsed signal. Instead, other shape energy profiles may be used, such as a Gaussian shape profile or a rounded profile.

The apparatus may also be used to assist in the tunneling process, i.e. the process of inserting the probe to the treatment region. The probe may be arranged to radiate microwave energy as the probe is inserted through the anatomical layers between the surface of the skin and the fat in order to form a channel for the antenna to be inserted without causing pain, preventing blood loss and reducing the level of discomfort experienced by the patient when the procedures are carried out using normal methods. In the tunneling process, it is desirable for the probe to produce focussed heat with a limited depth of penetration to heat the tissue structures in such a manner that a uniform channel is produced. Since there may be many different tissue structures on the path to the treatment region, sensitivity of the apparatus and dynamic adjustment of the power level may be required. To facilitate this, a measurement channel may be provided between the oscillator 108 and probe 104. The purpose of the measurement channel is to output low power signals at the probe which enable properties of any tissue present there to be measured. A power level for a signal through the treatment channel may be selected based on the measurements made using the measurement channel. This arrangement permits a uniform channel to be generated in the tissue.

The output from the splitter 110 on the measurement channel is received by a forward directional coupler 164 connected to couple power from measurement channel. The coupled port of the coupler 164 is connected to a switch 166, whose function is to select either the forward coupled or reflected coupled power under the control of the controller 114 to be conveyed for measurement by the heterodyne detector 126. The output of the forward directional coupler 164 on the measurement channel is received by the first port of a circulator 168, whose function is to isolate the reflected signals travelling back from the probe 104 from the source 102. Forward signals on the measurement channel travel from the first port of the circulator 168 to its second port, where they are output. Any reflected signals received at the second port of the circulator 168 travel to the third port and are output into a power dump load 170. The output from the second port of the circulator 168 is received by a directional coupler 172, which is configured as a forward power directional coupler and forms a part of a carrier cancellation circuit. The output from directional coupler 172 is fed into the first port of circulator 174. The second port of circulator 174 is connected to the probe 104 via switch 140. The third port of circulator 174 is connected to the input of a directional coupler 176, which is configured as a forward power directional coupler and forms a part of the carrier cancellation circuit. The function of the circulator 174 is to convey the reflected signal towards the heterodyne detector 126 whilst isolating the reflected signal from the forward signal. Forward signals on the measurement channel travel from the first port of the second circulator 174 to its second port, where they are output. Reflected signals from the probe 104 are received at the second port of the circulator 174, from where they travel to the third port and are output. The output of the third port of the circulator 174 is received by the directional coupler 176, which is part of the carrier cancellation circuit. After passing through the coupler 176, the reflected signal connected to the switch 166 is conveyed to the heterodyne detector 126 when selected.

The carrier cancellation circuit provides isolation in additional to that provided by the circulators 168, 174. The carrier cancellation circuit comprises the forward directional coupler 172, a phase adjuster 178, an adjustable attenuator 180, and a second forward directional coupler 176. The carrier cancellation circuit works by taking portion of the forward signal from the coupled port of coupler 172 and adjusting the phase and power level such that it is 180° out of phase out of phase and of the same amplitude as any unwanted signal that gets through to the third port of circulator 174 to enable the unwanted signal component to be cancelled out. The carrier cancellation signal is injected into the output of the third port of circulator 174 using second forward coupler 176.

Since the measurement channel provides reflected signals directly (i.e. not via a coupler) to the heterodyne detector 126 the power delivered on the measurement channel can be much less than that on the treatment channel.

Switches 140, 158 are arranged to switch together to select either the treatment or the measurement channel. The apparatus may periodically switch to the measurement channel during tunneling to monitor the tissue at the distal end of the probe. This measurement information may be used to enable appropriate adjustment of the energy profile (power level over specified durations of time) delivered into the biological tissue of interest. It may also be used as the basis for adjustment of the power matching network used to match the impedance of the end of the probe with the contact tissue, i.e. to ensure that the reflection coefficient is as close as possible to zero.

The arrangements of the directional couplers 122, 134 on the treatment channel provides an further advantage of this embodiment. Conventionally, forward and reverse couplers are inserted in the same path, e.g. between the output of the amplifier and the input to the probe. This can limit sensitivity of the measurement signals (or the dynamic range of the system) because it is possible for the unwanted signal to be of similar magnitude to the wanted (measurement) signal. This is particularly relevant when the reflected signal is small due to a small mismatch between the antenna and the load impedance. In this invention it may be important to make a measurement in this situation, e.g. where the system impedance is 50Ω and load impedance is 46Ω (i.e. in which 4.17% of the incident power is reflected back). The problem in this case is that an unwanted signal from a decoupled port that travels in the opposite direction from the wanted measurement signal can be of similar magnitude to the wanted signal, thus the measurement signal cannot be discerned from the noise signal. In conventional systems, the isolation between the forward and reverse signals is dependent only upon the coupling factor of the directional coupler (the sampled incident power) and the directivity (how well the coupler distinguishes between the forward and reverse travelling waves) and the total isolation (dB) between the forward and reverse signals equals the sum of the coupling factor (dB) and the directivity (dB).

This problem may be exacerbated in the invention when the reflected signal is used to control the energy delivery profile, because the reflected signal will be corrupted due to the fact that there will always be more forward signal than reflected signal due to path losses between the measurement coupler and the load, i.e. insertion loss of the cable and the antenna/probe shaft, etc.

The invention may overcome these problems in arrangements where there is no dynamic impedance matching or tuning by relocating the forward and reverse directional couplers to between the output of the power amplifier (or oscillator in the measurement channel) and the input to the first port of the circulator and between the third port of the circulator and the power dump load respectively.

Further increased isolation or enhanced measurement sensitivity between the forward and reverse signals may be achieved by inserting one or more additional circulators (with 50Ω dump loads connected between the third port and ground) between the forward signal coupler and the first port of the first circulator, with the final circulator being used to measure the reflected signal. Each additional circulator will increase the isolation in terms of the reverse power signal corrupting the forward power signal by the circulator unwanted power flow isolation, i.e. three additional circulators with isolation in unwanted path of 20 dB will increase the overall isolation by 60 dB.

FIGS. 3A, 3B and 3C shows cross-sectional side views of three exemplary probes for use with the apparatus discussed above.

FIG. 3A shows a probe 200 that comprises an elongate, pen-like body 202 having a connector 204 at its proximal end and an rounded tip 206 at its distal end. The connector 202 is connected to the flexible transmission cable 142 shown in FIG. 2. The body 202 has an integrated antenna, which comprises a coaxial feed structure that includes an inner conductor 206, an outer conductor 207 and a dielectric material 208 between them. The feed structure terminates with an aerial 209 at the round tip. The aerial 209 is arranged to radiate a microwave field.

In this embodiment, a conduit 203 is formed through the inner conductor 206. This arrangement makes use of the fact that the depth of penetration of a microwave field when energy propagates in conductive materials is very small (i.e. less than 0.1 mm). Thus, removing the centre of the inner conductor 206 to provide a conduit 203 for fat to be transported does not substantially affect transfer of the microwave energy. An additional advantage is that energy lost during the propagation in the coaxial feed structure may interact with fat in the conduit to gently heat it and maintain it in liquefied form.

The conduit 203 extends from an opening at the distal end of the probe (in this case an opening in the aerial 209) to an outlet located towards the proximal end of the probe. The flexible transport pipe 148 (as shown in FIG. 2) is connected to the outlet.

FIG. 3B shows a probe 210 that is similar to the probe 200 in FIG. 3A except that the conduit 213 is provided adjacent to the coaxial feed structure rather than through it. Components in common with FIG. 3A are given the same reference number and description thereof is not repeated. In this embodiment the inlet 212 to the conduit 213 is located to the side of the aerial 209. Although the inlet 212 is depicted as opening forwards, it may open sideways, i.e. the opening may run along the side of the probe.

FIG. 3C shows a probe 220 that is similar to the probe 200 in FIG. 3A except that the conduit 223 is an annular channel provided around the outside of the coaxial feed structure. Components in common with FIG. 3A are given the same reference number and description thereof is not repeated.

Figure 4:
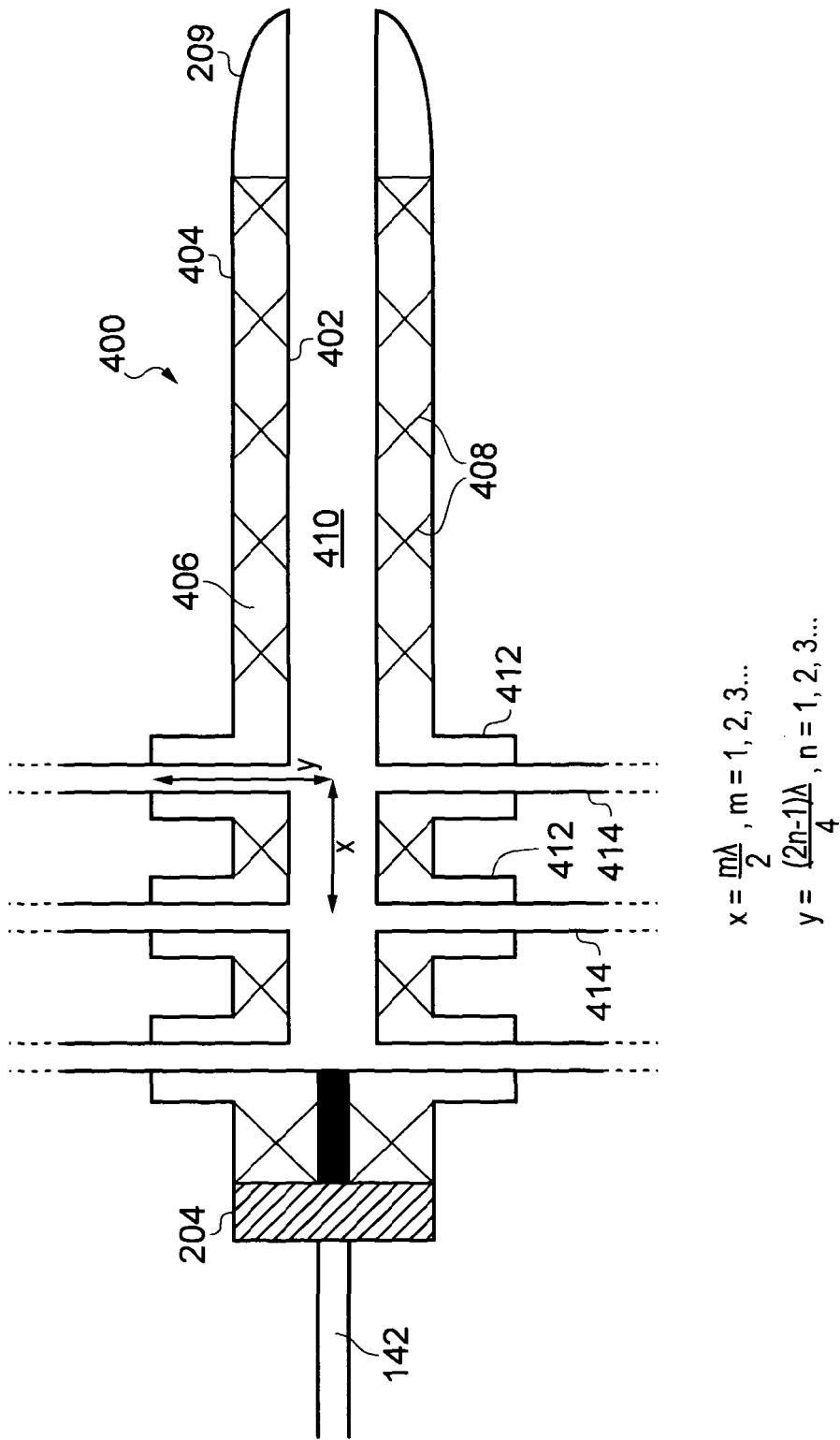
FIG. 4 is a schematic cross-sectional side view through a probe having multiple exit passages that is another embodiment of the invention.

FIG. 4 shows a probe 400 that is similar to the probe 200 is FIG. 3A. Components in common with FIG. 3A are given the same reference number and description thereof is not repeated. In this embodiment the inner conductor 402 is in the form of a hollow tube which formed the conduit 410 for extracting liquefied fat. The outer conductor 404 is separated from the inner conductor by a plurality of ring-like spacers 408, which are preferably made from a low loss dielectric material, i.e. PTFE. The spacers 408 may also be metallic, but, in this particular instance, it will be necessary for them to be located in such a manner that they do not affect the electromagnetic field set up within the structure, i.e. they should be located where the E-field is a minimum or at strategic positions along the structure where E-field minima occur. The dielectric material 406 of the coaxial feed structure in this embodiment is air.

The probe 400 has six exit passages 412 for transferring liquefied fat out of the conduit 410. Each exit passage 412 is a coaxial stub extending radially away from the conduit 410. Although the stubs are depicted as extending orthogonally to the axis of the coaxial feed structure, they may extend at any angle. Each stub may be coupled to a tube 414 connected to the suction device. The arrangement using a plurality of suction tubes may be advantageous in terms of enabling the flow of fat to increase, which may lead to a decrease in the treatment time. A further advantage is that this arrangement may prevent a pressure build up or a blockage occurring somewhere along the tube formed by the centre conductor.

At the distal end of each stub, the inner conductor 402 meets the outer conductor 404 to create a short circuit condition. To ensure a maximal electric field in the centre of the coaxial feed structure, the length of each stub, i.e. the distance from the axis of the feed structure to the end of the stub, is an odd multiple of quarter wavelengths, i.e.

$$\frac{(2n-1)\lambda}{4},$$

where n is any integer, and λ is the wavelength of the radiated microwave field. For microwave radiation having a frequency of 2.45 GHz, a quarter wavelength is about 3 cm.

Adjacent stubs may be spaced apart along the axis of the coaxial feed structure by a multiple of half wavelengths, i.e.

$$\frac{m\lambda}{2},$$

where m is any integer, and λ is the wavelength of the radiated microwave field. This may ensure that the magnitude of the field is at the same at the base of each stub. If the stubs each have a length that is an odd multiple of a quarter wavelength, it is desirable for the field to have a maximum magnitude at their respective bases to minimize loss in the fee structure. It should be noted that this arrangement is not limited to the use of $$\frac{m\lambda}{2}$$

spacing between adjacent stubs. The important factor is that E-field maxima are set up at the centre of the centre conductor using the feed arrangement described above, whereby E-field maxima are set up by shorting the inner and outer conductors a distance of quarter wavelength away from the centre conductor.

Figure 5:
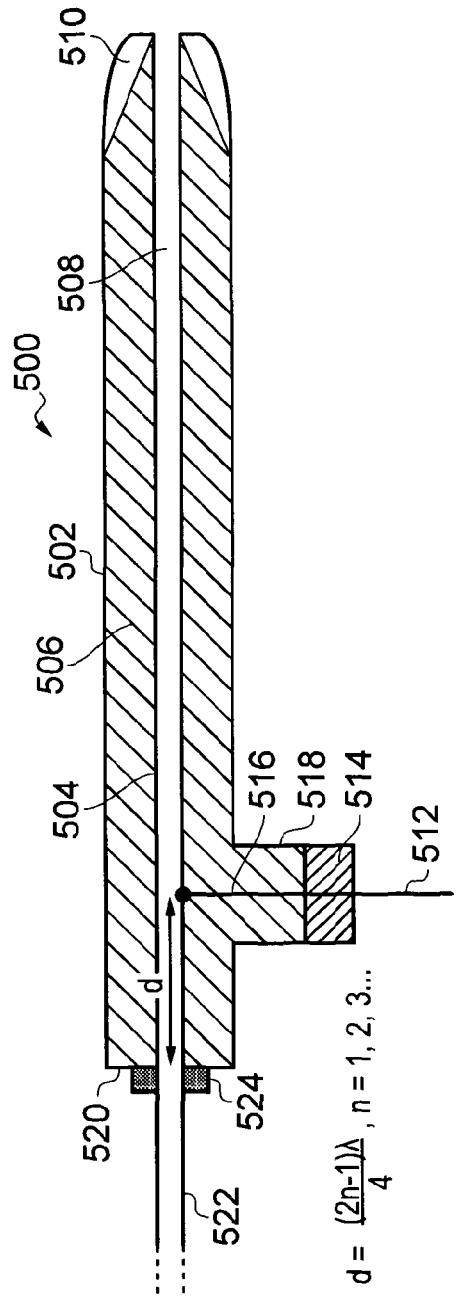
FIG. 5 is a schematic cross-sectional side view through a probe having a microwave power feed on its side that is another embodiment of the invention.

FIG. 5 shows a probe 500 for use with the present invention. The probe 500 has a coaxial feed structure that comprises an outer conductor 502 separated from an inner conductor 504 by a dielectric material 506. The inner conductor 504 is hollow to define a channel 508 for removing liquefied fat from a treatment site. The feed structure terminates at a distal end with an aerial 510 that is arranged to emit a focused microwave radiation field into tissue, e.g. fat at a treatment site, or blood en route. The aerial may be made from a hard dielectric (i.e. non-metallic) material to provide both structural strength and to enable a microwave radiation field to be emitted for treatment. The aerial 510 may be formed in a sharp point to aid insertion to the treatment site.

The probe 500 differs from previous embodiments in that the feed structure is side-fed, i.e. the microwave energy is delivered into the probe from a direction that is angled with respect to the axis of the feed structure, i.e. 90° to the axis. In FIG. 5, the microwave energy is delivered from a cable assembly 512 into the feed structure via a connector 514. The connector 514 may be conventional, e.g. N-type, SMA-type or and MCX. The connector 514 has a centre pin 516 that extends from the connector 514 through the dielectric material 506 to contact the inner conductor 504. The connector 514 also has a conducting outer sleeve 518 in electrical contact with the outer conductor 502. To ensure the energy feed is efficient, the inner conductor 504 (516) and outer conductor 502 (518) are brought into electrical contact with each other at a proximal end 520 of the probe 500 to create a short circuit condition, and the centre pin 516 contacts the inner conductor at a distance that is an odd multiple of a quarter wavelength from the short circuit location to produce an E-field maximum at this point.

An advantage of the side-fed arrangement is that the liquefied fat can be extracted along the axis of the coaxial structure, e.g. through a flexible extraction tube 522 attached at the proximal end 520 of the probe 500. The extraction path may thus be free from sharp corners, which may facilitate smooth flow. A plug 524 may be attached to seal around the interface between the probe 500 and extraction tube 522 to prevent leakage.

Figure 6:
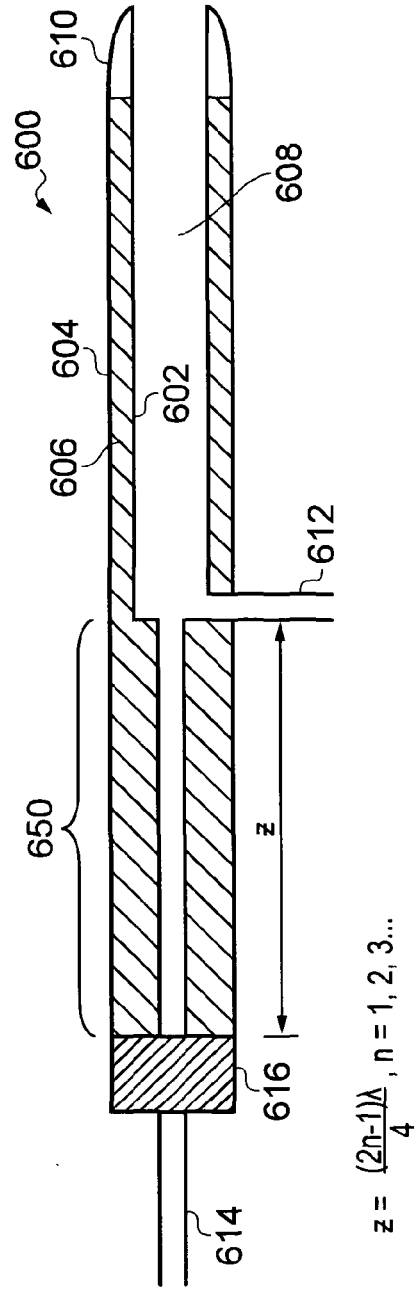
FIG. 6 is a schematic cross-sectional side view through a probe having an integral impedance transformer that is another embodiment of the invention.

FIG. 6 shows a probe 600 that has an integrally formed impedance transformer 650. The probe comprises a coaxial feed structure comprising an inner conductor 602 separated from an outer conductor 604 by a dielectric material 606. The inner conductor 602 is hollow to define a channel 608 for extracting liquefied fat from a treatment site. The coaxial structure terminates at its distal end with an aerial 610, e.g. made of a hard non-metallic material as discussed above. An extraction tube 612 is connected to the channel through the coaxial structure to convey the liquefied fat away from the probe.

In this embodiment, the distal section of the probe 600 that includes the channel may have an impedance that is matched to the impedance of biological tissue to be treated at the frequency of microwave energy conveyed by the coaxial structure. For example, the distal section may have an impedance arranged to match with adipose tissue or blood.

Typically, the impedance of tissue is less than the impedance of a standard microwave cable assembly (normally 50Ω). To ensure efficient deliver of microwave energy into the distal section, the probe 600 includes an impedance transformer 650. To ensure that the reflection coefficients at the junction between the source impedance (from the 50Ω cable assembly 614, connector 616 and the microwave generator) and impedance transformer 650 (characteristic impedance) and the distal section and impedance transformer 650 are minimised (preferably zero), the transformer 650 has a length of an odd multiple of quarter wavelengths of the microwave energy and an impedance $Z_T$ that satisfies the condition $$Z_T = \sqrt{Z_S Z_L},$$

where Zs is the source impedance (e.g. 50Ω) and $Z_L$ is the load impedance (i.e. impedance of the distal section), which is preferably also the same as the impedance of the tissue it encounters when its distal end makes either direct contact with the tissue, or makes contact via an aerial structure attached to the final coaxial structure.

Since the impedance of a coaxial feed structure depends on the relationship between the diameters of the inner and outer conductors, the impedance transformer can be integrated into a probe having a fixed outer diameter by suitable selection of the diameter of the inner conductor.

In detail, the impedance of a coaxial body may be expressed as:

$$Z = \frac{138}{\sqrt{\varepsilon_r}} \log \frac{b}{a},$$

where Z is the impedance of the coaxial body, $\varepsilon_r$ is the relative permittivity of the dielectric material separating the inner and outer conductors, a is the outer diameter of the inner conductor and b is the inner diameter of the outer conductor. To match a source impedance of 50Ω with a load impedance of 18Ω at 14.5 GHz, the impedance transformer may have a length of about 2 cm and an impedance of 30Ω. As shown in FIG. 6, this may be achieved by varying a and keeping $\varepsilon_r$ and b fixed.

A further antenna arrangement (not shown here) is an arrangement whereby the spacers or disks used to separate the inner and outer conductors, i.e. 408 in FIG. 4, are not made from solid materials, but contain gaps, e.g. holes or webbing, in order to provide a second channel to allow fat to flow between the inner wall of the outer conductor and the outer wall of the inner conductor, thus enable an increase in the volume of fat that can be transported along the structure. In this arrangement, the coaxial structure may be designed to take into account the average impedance of the fat and be set up to be an efficient transmission line when fat is present within the structure. Fat is a lossy material and so the fact that it now forms a part of the transmission line means that it may quickly heat up and stays liquefied to aid removal. It will also be possible to measure the impedance mismatch caused when no fat is present inside the structure and this information may be helpful or provide additional information to help control the system. This arrangement has the advantage of providing two channels that will increase the efficiency of the system when used in applications where it is necessary to remove large volumes of fat from the body.

Particular examples of semi-rigid co-axial cable assemblies that may be used to enable embodiments of the current invention shown in FIGS. 3A, 3B, 3C, 4 and 5 to be reduced to practice are:

1. Cable assembly part number: HC70009-3, available from Rhophase Microwave Ltd, which has an outside diameter of 2.1844 mm; and
2. Cable assembly with part numbers: UT85-0039 and UT47-0039, available from Rosenberger Micro-Coax Ltd, which have a maximum insertion loss of 1.32 dB per 100 mm length at an operating frequency of 46 GHz.

Figure 7:
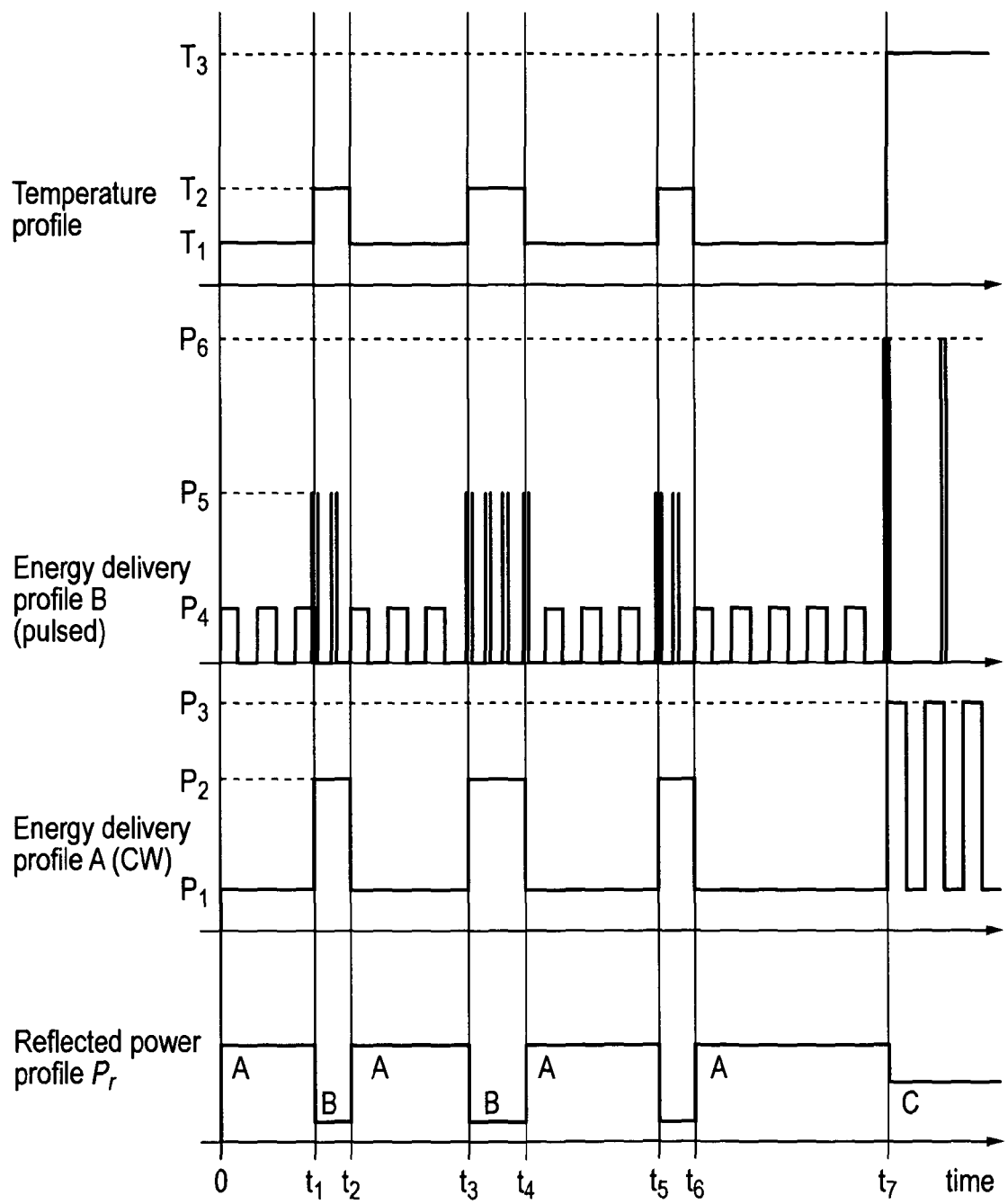
FIG. 7 is a chart showing the variation of reflected power, energy profile and tissue temperature over time during a method that is an embodiment of the invention.

FIG. 7 is a chart showing schematically how various parameters change with time during operation of the invention. The bottom line in FIG. 7 illustrates how the reflected power profile changes, i.e. how the magnitude of the reflected power detected by the detector changes, during treatment. In this embodiment, the reflected power exhibits three levels (A, B, C) where it is static, with abrupt transitions from one level to another at certain points in time. In this embodiment level A is exhibited when the probe is in fat and the radiated microwave field adopts its first configuration. Level B indicates a much lower level of reflected power. This may be associated with the lower reflection coefficient associated with blood, so level B is exhibited when the probe is in blood and the radiated microwave field adopts its second configuration. Level C is an intermediate level of reflected power, which in this embodiment may be associated with the presence of collagen at the distal end of the probe. Level C may thus be exhibited when the probe is in collagen and the radiated microwave field adopts its third configuration.

The top line in FIG. 7 illustrates schematically how the temperature of tissue at the distal end of the probe varies for the different types of tissue indicated by the reflection coefficient levels A, B and C discussed above. For fat, the temperature profile is relative low, e.g. 2° C.-3° C. above body temperature. For blood, the temperature profile is higher, e.g. 20° C.-30° C. above body temperature. For collagen it is higher still, e.g. 40° C.-50° C. above body temperature.

The temperature profiles illustrated in FIG. 7 are target profiles to be achieved by delivery of energy into the respective tissue types. The apparatus of the invention may be controllable to select an energy delivery profile (e.g. from a plurality of preset profiles) according to the detected reflected power profile or other information from the detector. FIG. 7 shows two examples of how energy profiles may be selected to achieve the desired temperature profile.

Example A relates to energy delivered by continuous wave (CW) transmission to the probe (i.e. where switch 116 in FIG. 2 is omitted or always closed). In this embodiment, the transition to reflected power level B is detected by the controller. Based on this detection, the controller adjusts the variable attenuator 112 to increase the output power level from $P_1$ to $P_2$. In combination with the microwave field automatically adopting its second configuration (where delivered power is focussed tightly into blood), this facilitates coagulation. When the blood vessel is sealed, the reflected power returns to level A. This is detected by the controller, which adjusts the variable attenuator 112 to decrease the output power level from $P_2$ to $P_1$ to coincide with the microwave field automatically adopting its first configuration. Similar adjustments occur whenever a burst blood vessel is encountered.

At the end of the liposuction process (i.e. after the fat is removed), the probe may be moved to the collagen. The controller detects the presence of collagen at the distal end of the probe from the transition to level C in the reflected power level. Based on this detection, the controller adjusts the variable attenuator 112 to increase the output power level from $P_1$ to $P_3$ for a plurality of short bursts. In combination with the microwave field automatically adopting its third configuration (where delivered power is focussed tightly into collagen), this raises the temperature of the collagen to a level which facilitates skin tightening.

Example B relates to energy delivered by pulsed wave transmission to the probe. The method corresponds to that discussed with respect to example A, except that the controller also controls the switch 116 to determine the pulse length and separation (duty cycle). For example, the pulses may be more spaced out when treating fat in order to keep the temperature relatively low. In contrast, the pulses may be closely spaced when treating blood. When treating collagen, the pulses may have very high amplitude but a wide separation (e.g. 30% duty cycle), whereby the energy is delivered very quickly into the collagen to create the necessary instantaneous heat that is highly focussed into the collagen and causes no damage to adjacent tissue structures.

The invention claimed is:
1. Surgical apparatus thr liposuction comprising:
   a microwave energy source arranged to Output a controllable power level of microwave radiation;

a probe for inserting to a treatment region in biological tissue, the probe including:
  an antenna connected to receive the output microwave radiation and arranged to emit outwardly a microwave radiation field to deliver microwave energy in the treatment region, and
  a conduit for conveying liquefied fat away from the treatment region;
a suction pump connected to the conduit;
a detector arranged to detect forward microwave power delivered to the probe; and
a controller for adjusting the controllable power level of microwave radiation,
wherein the detector is arranged to detect microwave power reflected back from the treatment region;
the controller is arranged to select an energy delivery profile from a plurality of predetermined energy delivery profiles based on changes in the detected reflected microwave power based on the detected forward and reflected microwave power to deliver microwave energy according to a predetermined energy delivery profile; and
the apparatus further comprises:
  a variable attenuator controlled by the controller for varying the amplitude of the microwave radiation from the microwave energy source according to the selected energy delivery profile; and
  a switch controlled by the controller for modulating the microwave radiation from the microwave energy source to enable pulsed or continuous wave operation according to the selected energy delivery profile,
wherein the plurality of predetermined energy delivery profiles include energy delivery profiles in which the frequency of the microwave radiation and the controllable power level are selected such that the emitted microwave radiation field automatically adopts a first configuration when emitted into fat and a second configuration when emitted into blood, the microwave energy delivered by first configuration being for liquefying the fat and the microwave energy delivered by the second configuration being for coagulating the blood.

2. Surgical apparatus according to claim 1, wherein the frequency of the microwave radiation and the controllable power level are both the same in the first and second configurations.

3. Surgical apparatus according to claim 1, wherein the first and second configurations are arranged to cause a temperature increase in fat and blood respectively, the temperature increase caused by the second configuration in blood being an order of magnitude greater than the temperature increase caused by the first configuration in fat.

4. Surgical apparatus according to claim 1, wherein the frequency of the microwave radiation is 5 GHz or more.

5. Surgical apparatus according to claim 1, wherein the plurality of predetermined energy delivery profiles include an energy delivery profile in which the controllable power level of microwave radiation is selected to cause the emitted microwave radiation field to adopt a third configuration when emitted into collagen, the third configuration being for tightening the collagen.

6. Surgical apparatus according to claim 1 including a circulator connected between the source, probe and detector, wherein a forward path for microwave energy from the source passes from a first port to a second port of the circulator, a reflected path for microwave energy from the probe passes from the second port to a third port of the circulator, and the detector includes a first directional coupler connected to couple power output from the third port of the circulator.

7. Surgical apparatus according to claim 6, wherein the detector includes a second directional coupler connected to couple power input to the first port of the circulator.

8. Surgical apparatus according to claim 7, wherein one or more additional circulator are connected between the second directional coupler and the circulator to increase isolation between the forward and reflected paths.

9. Surgical apparatus according to claim 1, wherein the frequency of the microwave energy is adjustable.

10. Surgical apparatus according to claim 1, wherein the conduit is integrated with the antenna.

11. Surgical apparatus according to claim 1, wherein the antenna comprises a single conductor waveguide structure including a hollow outer conductor filled with a dielectric loading material, and wherein the conduit is integrated into the waveguide structure such that the liquefied fat constitutes all or some of the loading material.

12. Surgical apparatus according to claim 1, wherein the antenna comprises a coaxial structure having an inner conductor and an outer conductor, and the conduit includes a cavity between the inner and outer conductors.

13. Surgical apparatus according to claim 1, wherein the antenna includes a coaxial feed structure comprising an inner conductor separated from an outer conductor by a dielectric material, and an aerial that terminates the coaxial feed structure at a distal end of the probe, and wherein the conduit includes a hollow tube in the inner conductor of the coaxial feed structure.

14. Surgical apparatus to according to claim 9, wherein the aerial is an omni-directional radiator.

15. Surgical apparatus according to claim 1 including a static coaxial impedance transformer inserted between the microwave energy source and the antenna to enable the impedance of the antenna to be adjustable to match the impedance of the fat encountered at the distal end of the antenna.

* * * * *